United States Patent [19]
König et al.

[11] Patent Number: 4,900,658
[45] Date of Patent: Feb. 13, 1990

[54] CHROMOPHORIC PEPTIDES FOR DETECTING PEPTIDYLGLYCINE-α-AMIDIZING MONOOXYGENASE

[75] Inventors: Wolfgang König, Hofheim am Taunus; Hubert Müllner, Kelkheim; Jan Glauder, Frankfurt am Main, all of Fed. Rep. of Germany

[73] Assignee: Hoechst Aktiengesellschaft, Frankfurt, Fed. Rep. of Germany

[21] Appl. No.: 36,468

[22] Filed: Apr. 9, 1987

[30] Foreign Application Priority Data

Apr. 11, 1986 [DE] Fed. Rep. of Germany ....... 3612302

[51] Int. Cl.$^4$ .......................... C12Q 1/00; C12Q 1/34; C07K 5/08; C07K 5/06
[52] U.S. Cl. .......................................... 435/4; 435/18; 435/24; 435/25; 530/331; 530/335; 530/802
[58] Field of Search .................... 435/4, 15, 18, 24, 25, 435/70; 530/331, 335, 802

[56] References Cited

U.S. PATENT DOCUMENTS

| | | | |
|---|---|---|---|
| 4,203,967 | 5/1980 | Gallo-Torres | 424/9 |
| 4,222,743 | 9/1980 | Wang | 436/800 |
| 4,563,305 | 1/1986 | Ryan et al. | 530/802 X |
| 4,708,934 | 11/1987 | Gilligan et al. | 435/68 |
| 4,758,520 | 7/1988 | Matuszewski et al. | 426/89 X |

OTHER PUBLICATIONS

G. S. Wand, R. L. Ney, R. E. Mains, B. A. Eipper, Neuroendocrinology, vol. 41, pp. 482–489 (1985).
B. A. Eipper, A. C. Myers, R. E. Mains, Endocrinology, vol. 116, No. 6, pp. 2497–2504 (1985).
G. S. Wand, R. L. Ney, S. Baylin, B. Eipper, R. E. Mains, Metabolism, vol. 34, No. 11, pp. 1044–1052 (1985).

Primary Examiner—David M. Naff
Attorney, Agent, or Firm—Finnegan, Henderson, Farabow, Garrett and Dunner

[57] ABSTRACT

A chromophoric peptide is prepared of the formula

DIS—D—Ala-Pro-R and salts thereof in which R represents Gly-OH, NH$_2$ or Gly-R$^2$ wherein R$^2$ denotes a carboxyl protective group, and DIS denotes 5-dimethylaminonaphthalene-1-sulfonyl. The enzyme, peptidylglycine-α-amidizing monooxygenase, is quantitatively detected by contacting a sample containing the enzyme with the peptide of the above formula when R denotes Gly—OH, separating a resultant peptide of the above formula when R denotes NH$_2$ and determining the amount thereof quantitatively. When R is Gly—R$^2$, the protective group R$^2$ is removed to produce the peptide when R is Gly—OH. Advantages of the peptide are that C-terminal degradation caused by carboxypeptidases is rendered more difficult by the incorporation of proline, and the peptide contains a fluorescent group.

5 Claims, No Drawings

CHROMOPHORIC PEPTIDES FOR DETECTING PEPTIDYLGLYCINE-α-AMIDIZING MONOOXYGENASE

The invention relates to chromophoric peptides of the general formula I $$\text{DIS—D—ALa—Pro—R} \qquad (I)$$

in which R represents Gly—OH or $NH_2$ and DIS denotes 5-dimethylamino-naphthalene-1-sulfonyl, and salts thereof.

Suitable salts are, in particular, salts of alkali and alkaline earth metals, salts with amines and salts with inorganic or organic acids, such as, for example, hydrochloric acid, hydrobromic acid, sulfuric acid, maleic acid or fumaric acid.

Peptidylglycine-α-amidizing monooxygenase (PAM) is an important enzyme which forms the corresponding peptide amides from peptides containing C-terminal glycine (peptidylglycine). In the case of many peptide hormones, such as, for example, gonadoliberin, thyroliberin, secretin or calcitonin, the amidized form is the more active. However, only peptides containing neutral C-terminal amino acids are amidized (A. F. Bradbury, M. D. A. Finnie and D. G. Smyth, Nature 298 (1982) 686–688).

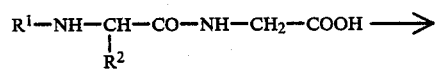

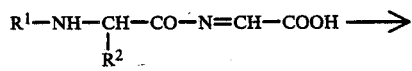

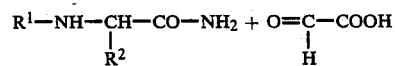

Thus it has been found that this enzyme is responsible, for example, for the formation of the thyrotropin-releasing factor (TRH) (I. Husain and S. S. Tate, FEBS Letters 152 (1983) 277–281; J. S. Kizer, W. H. Busby, Jr., C. Cottle and W. W. Youngblood, Proc. Natl. Acad. Sci. USA 81 (1984) 3228–3232; S. Gomez, C. di Bello, L. T. Hung, R. Genet, J.-L. Morgat, P. Formageot and P. Cohen, FEBS Letters, 167 (1984) 160) and of α-melanotropin (α-MSH) (C. C. Glembotski, J. Biol. Chem. 259 (1984) 13041–13048).

This monoxygenase is dependent on ascorbic acid, copper ions and oxygen and is formed wherever peptide amides are set free. Hitherto, peptidylglycine-α-amidizing mono-oxygenase has been found, above all, in the pituitary gland and in the central nervous system. This enzyme can, however, also be detected in the plasma. In tumors which form peptide amides, the activity of the enzyme in the plasma is considerably increased and it can thus serve as a marker for certain endocrine tumors.

The activity of this enzyme can be measured by the conversion:

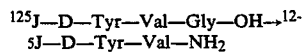

(G. S. Wand, R. L. Ney, R. E. Mains, B. A. Eipper, Neuroendocrinology 41 (1985) 482–489; B. A. Eipper, A. C. Myers and R. E. Mains, Endocrinology 116 (1985) 2497–2504; G. S. Wand, R. L. Ney, S. Baylin, B. Eipper and R. E. Mains, Metabolism 34 (1985) 1044–1052).

In order to avoid the necessity of working with radioactive substances, a new method for the determination of peptidylglycine-α-amidizing activity has been sought.

This problem has been solved by means of a fluorescent substrate which can be isolated and identified by chromatographic methods (thin layer and high-pressure liquid chromatography). In addition to the advantage of its fluorescent 5-dimethylaminonaphthalene-1-sulfonyl-(DIS-) group, DIS—D—Ala—Pro—Gly—OH according to the invention also has the merit that C-terminal degradation caused by carboxypeptidases is rendered more difficult by the incorporation of proline. DIS—D—Ala—Pro—$HN_2$ serves as a comparison.

The invention also relates to a process for the preparation of a peptide of the formula I, which comprises reacting a compound of the formula II $$\text{DIS—Hal} \qquad (II)$$

in which
DIS denotes 5-dimethylamino-naphthalene-1-sulfonyl and Hal denotes halogen, preferably chlorine, with a compound of the formula III $$\text{H—D—Al—Pro—R}^1 \qquad (III)$$

in which
$R^1$ denotes Gly—$R^2$ or $NH_2$ and
$R^2$ denotes a carboxyl protective group,
in the event that $R^1$ denotes Gly—$R^2$, splitting off the carboxyl protective group from the compounds of the formula IV thus obtained, with the formation of the free carboxyl group, and, if appropriate, converting the peptide of the formula I thus obtained into its salts.

Examples of suitable carboxyl protective groups $R^2$ are described in Schroöder, Lübke, The Peptides, Volume I, New York 1965, pages 72–75 or in T. W. Greene, "Protective Groups in Organic Synthesis", Wiley-Interscience, New York 1981. Suitable groups are lower alkyl groups, such as methyl, ethyl or tert.-butyl, and aralkyl groups, such as benzyl or p-nitrobenzyl; tert.-butyl is preferred. The elimination of the protective group from the intermediate products of the formula IV $$\text{DIS—D—Ala—Pro—R}^1 \qquad (IV)$$

in which $R^1$ represents Gly—$R^2$ and DIS and $R^2$ are as defined above, is effected, depending on the nature of the protective group, by alkaline or acid hydrolysis or by hydrogenolysis. The substrate DIS—D—Ala—Pro—Gly—OH according to the invention is preferably obtained from the corresponding tert.-butyl ester by an acid treatment. The peptides of the formula III mentioned above can be prepared by the general methods of peptide chemistry, for example by coupling appropriate fragments, if appropriate protected fragments, in the presence of dicyclohexylcarbodiimide and, if appropriate, 1-hydroxy-1H-benzotriazole in a suitable solvent (cf. Chem. Ber. 103 [1970] 788, 2024).

The invention also relates to a process for the qualitative or quantitative detection of peptidylglycine-α-amidizing monooxygenase, which comprises incubating a solution of the formula I in which R denotes Gly—OH with the analytical sample containing peptidylglycine- α-amidizing monooxygenase, separating off the resulting compound of the formula I in which R denotes $NH_2$ and determining the amount thereof quantitatively, and to the use of a compound of the formula I for the qualitative or quantitative detection of peptidylglycine-α-amidizing monooxygenases, agents containing a compound of the formula I and intermediate products of the formula IV in which DIS denotes 5-dimethylamino-naphthalene-1-sulfonyl, $R^1$ denotes Gly—$R^2$ and $R^2$ denotes a carboxyl protective group.

The enzyme (PAM) was isolated from bovine pituitary glands by a method of Eipper et al. (Peptides 4, (1983) 921-928). In this method, fresh pituitary glands were homogenized in tris buffer, the homogenate was separated via a Percoll gradient centrifugation process and the vesicle fraction was isolated. It was possible to detect the highest activity in this fraction. The activity could be enriched further by ammonium sulfate precipitation and consecutive gel filtration (Glembotski, Arch. Biochem. Biophys. 241 (1985) 673-683). The tests with the substrate, according to the invention, of the formula I (R=Gly—OH) and with the comparison substance of the formula I (R=$NH_2$) were carried out both with the crude fractions and also with the enriched fractions.

The examples below serve to illustrate the invention, without limiting the latter thereto.

EXAMPLE 1

DIS—D—Ala—Pro—Gly—OH (a) Z—D—Ala—Pro—Gly—OBut 6.54 ml of N-ethylmorpholine and 10.7 g of DCC are added at 0° C. to a solution of 11.4 g of Z—D—Ala—OH, 13.5 g of H—Pro—Gly—OBut.HCl and 6.9 g of HOBt in 100 ml of dimethylformamide. The mixture is stirred for 1 hour at 0° C. and 4 hours at room temperature and is allowed to stand overnight at room temperature. The precipitate is filtered off with suction and the filtrate is concentrated. The residue is partitioned between ethyl acetate and water. The ethyl acetate phase is extracted by shaking successively with saturated aqueous $NaHCO_3$ solution, $KHSO_4/K_2SO_4$ buffer and water, dried over $Na_2SO_4$ and concentrated. The substance is chromatographed over 300 g of silica gel (1. $CH_2Cl_2$/acetone in a 9:1 ratio; 2. $CH_2Cl_2/CH_3OH$ in a 9.6:0.4 ratio). Yield of pure amorphous substance: 10.3 g.

(b) H—D—Ala—Pro—Gly—OBut.HCl 10 g of Z—D—Ala—Pro—Gly—OBut are dissolved in 100 ml of methanol and hydrogenated over a Pd catalyst at a controlled pH (autotitrator with methanolic HCl at pH 4.5). When hydrogenation is complete (monitored by thin-layer chromatography in $CH_2Cl_2/CH_3OH$ in a ratio of 9:1), the catalyst is filtered off with suction and the filtrate is concentrated. The residue is 6.2 g of a colorless amorphous substance.

(c) DIS—D—Ala—Pro—Gly—OBut 1.4 ml (10 mmol) of triethylamine are added at −5° C. to a suspension of 1.68 g (5 mmol) of H—D—Ala—Pro—Gly—OBut.HCl and 1.4 g (5.2 mmol) of DIS-chloride in 25 ml of absolute tetrahydrofuran. The mixture is stirred for 1 hour at 0° C. and 4 hours at room temperature and is allowed to stand overnight at room temperature. The precipitate is filtered off with suction and the filtrate is concentrated. The residue is dissolved in ethyl acetate. The solution is extracted by shaking successively with saturated aqueous $NaHCO_3$ solution and water, dried over $Na_2SO_4$ and concentrated.

Yield: 3.5 g of amorphous substance.

(d) DIS—D—Ala—Pro—Gly—OH

A solution of 3.5 g of DIS—D—Ala—Pro—Gly—OBut in 10 ml of 90% strength trifluoroacetic acid is allowed to stand at room temperature for 1 hour. The solution is then concentrated in vacuo. The residue is 3.2 g of an amorphous substance. 300 mg was purified by chromatography over a silica gel column (40×4 cm). Mobile phase: $CH_2Cl_2/CH_3OH/CH_3COOH/H_2O$ in a ratio of 9:1:0.1:0.1. The fractions containing the pure substance are concentrated. The residue is dissolved in water and freeze-dried.

Yield: 191 mg; $[\alpha]_D^{24} = -51.8°$ (c=1, in 5% strength aqueous solution acetic acid).

$^1$H-NMR (270 MHz) in $^2$H-DMSO: characteristic signals at $\delta = 1.0$ [d, 3H, —$CH_3$ (Ala)]; 2.83 [2s, 6H, —$N(CH_3)_2$ (DIS)]; 3.7 [d, 2H, —$CH_2$— (Gly)]; 7.25-8.5 [d, m, 8H (2=NH and 6 aromatic H of DIS)].

EXAMPLE 2

DIS—D—Ala—Pro—$NH_2$ (a) Z—D—Ala—Pro—$NH_2$ 6.4 ml (50 mmol) of N-ethylmorpholine and 11.4 g (55 mmol) of dicyclohexylcarbodiimide (DCC) are added at 0° C. to a solution of 11.2 g (50 mmol) of Z—D—Ala—OH, 7.53 g (50 mmol) of H—Pro—$NH_2$.HCl and 6.8 g (50 mmol) of HOBt in 100 ml of dimethylformamide. The mixture is stirred for 1 hour at 0° C. and 5 hours at room temperature and is allowed to stand overnight at room temperature. The precipitate is filtered off with suction and the filtrate is concentrated. The residue is partitioned between ethyl acetate and water. The ethyl acetate phase is washed successively with saturated aqueous $NaHCO_3$ solution and $KHSO_4/K_2SO_4$ buffer, dried over $Na_2SO_4$ and concentrated. The residue is digested several times with petroleum ether, and the extract is them chromatographed over 180 g of silica gel ($CH_2Cl_2/CH_3OH$ in a ratio of 9.5:0.5). Yield of pure peptide: 6.74 g of colorless amorphous substance.

(b) H—D—Ala—Pro—$NH_2$.HCl 6.4 g (20 mmol) of Z—D—Ala—Pro—$NH_2$ are dissolved in methanol and hydrogenated catalytically as in 1b. The residue is triturated with ether.

Yield: 4.11 g of a colorless substance.

(c) DIS—D—Al—Pro—$NH_2$ 0.56 ml (4 mmol of triethylamine are added at 0° C. to a suspension of 0.442 g (2 mmol) of H—D—Ala—Pro—$NH_2$ and 0.6 g (2.2 mmol) of DIS-chloride in 15 ml of absolute tetrahydrofuran. The mixture is stirred for 1 hour at 0° C. and 5 hours at room temperature and is allowed to stand overnight at room temperature. It is worked up as in 1c and purified over silica gel (40×4 cm; mobile phase $CH_2Cl_2/CH_3OH$ in a ratio of 9.5:0.5).

Yield of pure substance: 0.23 g $[\alpha]_D^{24} = -18.4°$ (c=1, in 5% strength aqueous acetic acid).

$^1$H-NMR (270 MHz) in $^2$H-DMSO: characteristic signals at $\delta = 0.97$ [d, 3H, —$CH_3$ (Ala)]; 2.83 [2s, 6H, —$N(CH_3)_2$ (DIS)]; 6.9-8.5 [d, m, 9H, 3=NH and 6 aromatic H of DIS].

EXAMPLE 3

Procedure for enzyme assay using the substrate of the formula I (R=Gly—OH) and the reference substance of the formula II (R=$NH_2$)

The enzyme tests are carried out in a buffer of pH 7.4. The aqueous buffer is composed of the buffer substance N-[tris-(hydroxymethyl)-methyl]-2-amino-ethanesulfonic acid (100 mM), $CuSO_4$ (3 μM), peptide substrate of the formula I (R=Gly—OH) (50 μM) and catalase from bovine liver (100 μg/ml). 100 μl of this buffer solution are incubated with 100 μl of the solution containing PAM, and, after 3 hours at 37° C., the reaction is stopped by adding 700 μl of $CH_2Cl_2$. The peptide amide is transferred selectively into the organic phase by brief extraction by shaking (extraction yield: approx. 60%). After the mixture has been centrifuged and the organic phase removed, the latter is evaporated in a vacuum centrifuge and the residue is again taken up in a constant volume of $CH_2Cl_2$. All operations are carried out with exclusion of light in order to prevent photoreactions of the light-sensitive substrate. The resulting solutions are applied to HPTLC plates (Merck Si 60) by means of an auto-spotter, and separation is carried out using a mobile phase mixture ($CH_2Cl_2$/$CH_3OH$/$H_2O$/$CH_3COOH$ in a ratio of 90:10:1:1). Quantification of the resulting amide of the formula I (R=$NH_2$) by means of a thin layer scanner is made possible by simultaneously applying the peptide amide of the formula II in various concentrations as a reference.

| Conversion of DIS-D-Ala—Pro—Gly—OH having PAM activity as a function of time | | | |
|---|---|---|---|
| t (minutes) | 60 | 120 | 180 |
| Formation of peptide amide (ng) | 21.5 | 43.8 | 67.5 |

After 3 hours approx. 5%. of the substrate of the formula I (R=Gly—OH) have reacted at a conversion rate of 0.29 ng/hour per 1 μg of added protein having PAM activity.

We claim:

1. A peptide of the formula V

DIS—D—Ala—Pro—Q        (V)

and salts thereof in which
   DIS denotes 5-dimethylaminonaphthalene-1-sulfonyl,
   Q denotes Gly—OH, $NH_2$ or Gly—$R^2$ and
   $R^2$ denotes a carboxyl protective group.

2. A peptide of the formula V, as claimed in claim 1, in which Q denotes Gly—OH or $NH_2$, and salts thereof.

3. A peptide of the formula V, as claimed in claim 1, wherein
   Q denotes Gly—$R^2$ and
   $R^2$ denotes a carboxyl protective group.

4. A process for the qualitative of quantitative detection of peptidylglycine-α-amidizing monooxygenase, which comprises incubating a solution of a peptide of the formula DIS—D—Ala—Pro—Gly—OH, wherein DIS denotes 5-dimethylaminonapthalene-1-sulfonyl, with an analytical sample containing peptidylglycine-α-amidizing monooxygenase, separating a resulting peptide of the formula DIS—D—Ala—Pro—$NH_2$, wherein DIS is as denoted above, and determining the amount thereof quantitatively.

5. A composition containing a peptide of the formula

DIS—D—Ala—Pro—Q and salts thereof in which DIS denotes 5-dimethylaminonaphthalene-1-sulfonyl and Q denotes Gly—OH or $NH_2$, said peptide being in an amount effective for the qualitative or quantitative detection of peptidylglycine-α-amidizing monooxygenase and said peptide being in combination with a buffer.

* * * * *